United States Patent
Bostick et al.

(10) Patent No.: US 10,782,715 B2
(45) Date of Patent: Sep. 22, 2020

(54) BIOMETRIC ENCLOSURE TEMPERATURE CONTROL

(71) Applicant: International Business Machines Corporation, Armonk, NY (US)

(72) Inventors: James E. Bostick, Cedar Park, TX (US); John M. Ganci, Jr., Cary, NC (US); Martin G. Keen, Cary, NC (US); Brian M. O'Connell, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/281,038

(22) Filed: Feb. 20, 2019

(65) Prior Publication Data

US 2019/0196522 A1 Jun. 27, 2019

Related U.S. Application Data

(63) Continuation-in-part of application No. 15/853,334, filed on Dec. 22, 2017.

(51) Int. Cl.
*G05D 23/19* (2006.01)
*G05D 23/20* (2006.01)
*A61H 33/00* (2006.01)

(52) U.S. Cl.
CPC ..... *G05D 23/1931* (2013.01); *A61H 33/0095* (2013.01); *G05D 23/19* (2013.01);
(Continued)

(58) Field of Classification Search
CPC ...... A61M 2205/3368; A61M 2230/50; A61M 2005/1726; A61M 2021/0066;
(Continued)

(56) References Cited

U.S. PATENT DOCUMENTS 9,473,321 B1 * 10/2016 Bazar ................. H04L 12/2803
2003/0080194 A1 5/2003 O'Hara et al.
(Continued)

FOREIGN PATENT DOCUMENTS

JP 2014173752 9/2014

OTHER PUBLICATIONS

Unknown, "Hot Tubs Can Land Your Heart in Hot Water," https://health.clevelandclinic.org/2014/07/hot-tubs-can-land-your-heart-in-hot-water/, printed Jan. 22, 2020, 2 pgs.
(Continued)

*Primary Examiner* — Michael J Brown
(74) *Attorney, Agent, or Firm* — Grant Johnson

(57) ABSTRACT

Embodiments of the present invention provide a method, system and computer program product for biometric enclosed space control. A method for biometric enclosed space control includes establishing a set point for an enclosed space and electronically transmitting a directive to a temperature control system to temperature regulate an atmosphere in the enclosed space to maintain a temperature of the atmosphere at the set point. The method also includes detecting a presence of an end user in the enclosed space and remotely sensing biometric measurements of the end user while the end user remains in the enclosed space. Finally, the method includes electronically transmitting a directive to the temperature control system to change the set point in response to a most recently received one of the remotely sensed biometric measurements.

20 Claims, 1 Drawing Sheet

(52) U.S. Cl.
CPC ..... *G05D 23/20* (2013.01); *A61H 2201/5082* (2013.01); *A61H 2230/06* (2013.01); *A61H 2230/425* (2013.01)

(58) Field of Classification Search
CPC ...... A61M 2205/33; A61M 2205/3592; A61M 2230/06; A61M 2230/30; G05B 15/02; G05B 2219/2642; G05D 23/1931; G05D 23/19; G05D 23/20; A61H 33/0095; A61H 2230/425
USPC .......................................................... 700/90
See application file for complete search history.

(56) References Cited

U.S. PATENT DOCUMENTS

| | | | |
|---|---|---|---|
| 2008/0223788 A1* | 9/2008 | Rimdzius | A61H 33/06 210/664 |
| 2009/0255049 A1 | 10/2009 | Rosenau | |
| 2014/0067130 A1 | 3/2014 | Pillai et al. | |
| 2015/0064314 A1 | 3/2015 | Manuel et al. | |
| 2016/0239624 A1 | 8/2016 | Short et al. | |

OTHER PUBLICATIONS

Boone, et al., "Cardiovascular responses to a hot tub bath," Journal of Alternative and Complementary Medicine, vol. 5, No. 3, pp. 301-304, 1999.

\* cited by examiner

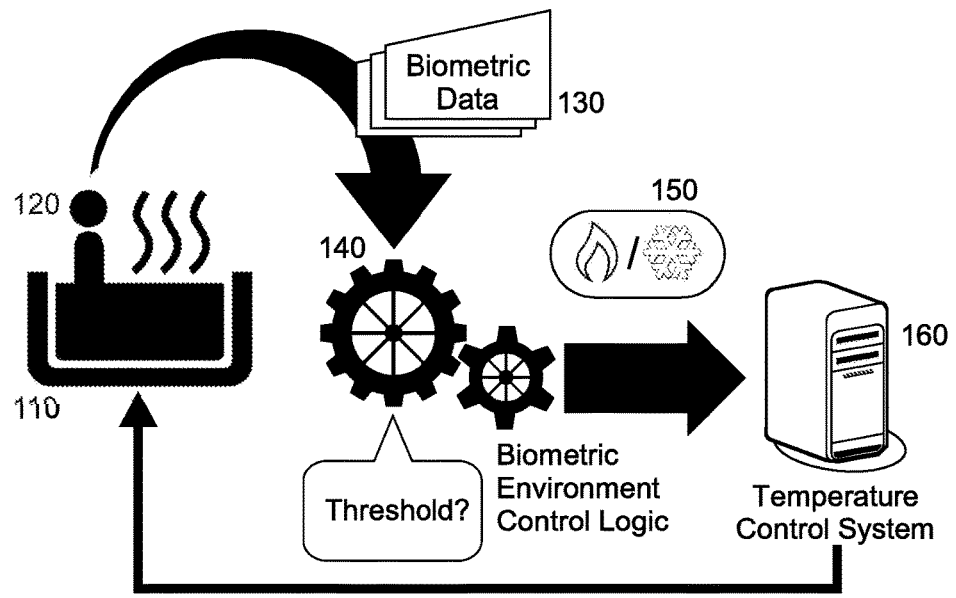
FIG. 1
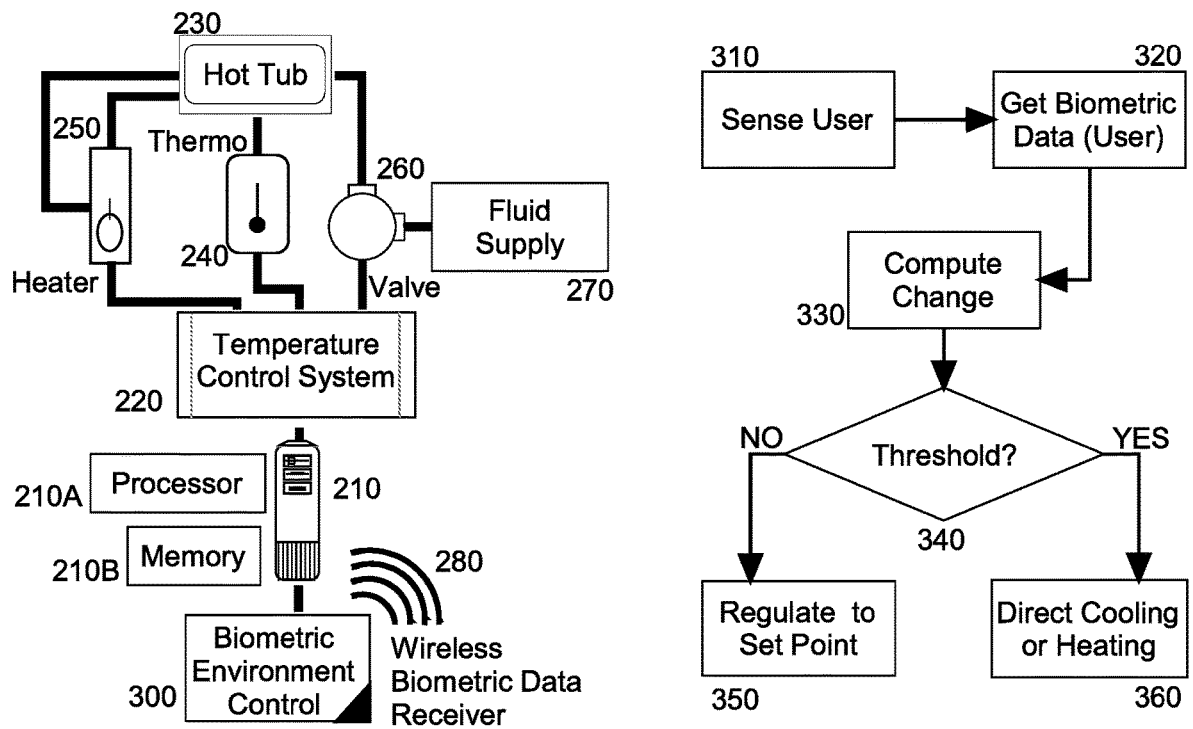
FIG. 2  FIG. 3

BIOMETRIC ENCLOSURE TEMPERATURE CONTROL

BACKGROUND

Field of the Invention

The present invention relates to temperature control systems and more particularly to the management of temperature in an enclosure.

Description of the Related Art

Shelter refers to the act of receiving protection from the elements of the environment. Typically, with respect to an enclosed space such as a room or reservoir, or any partially or fully enclosed space, as well as any receptacle or vessel that can retain a fluid, such as aquariums, terrariums, hot tubs, pools, and the like, shelter can be both relieving and concerning. While protecting one from the uncomfortable nature of the natural environment including extreme temperatures and weather, an enclosed space also presents new challenges in environmental control. In particular, to the extent that an enclosed space presents an insulative effect, preventing heat transfer between an interior portion of the enclosed space and the exterior portion, an enclosed space presents an opportunity for a rapid heating of the interior environment so as to create a risk for an individual within the enclosed space of heat stress.

In this regard, when an individual enters a heated enclosed space, the temperature of the body of the individual rises. However, the blood pressure of the body drops. Evaporating sweat normally assists in the cooling of the body, but not in an enclosed space where the rise in temperature outpaces the ability of the act of sweating to reduce internal body temperature. When super-heated, blood diverts to the skin, blood vessels dilate to help the body cool and heart rate and pulse increase to counteract the drop in blood pressure. Symptoms of skin problems, dizziness, nausea, and various heart issues result. Medications prescribed for heart conditions also contribute to the foregoing symptoms. For example, diuretics increase excretion of water and salt.

To counteract the detrimental effect of excessive heating in an enclosed space, an obvious solution is to simply adjust the temperature of the enclosed space to a lower temperature. Indeed, many thermostatic controllers for heated enclosed spaces include a timed operation in which the heating of the enclosed space occurs only for a select period of time before the heating stops. But knowing when to reduce the temperature of the enclosed space and for what duration remains variable and unknown to the end user.

SUMMARY

Embodiments of the present invention address deficiencies of the art in respect to enclosed space temperature management and provide a novel and non-obvious method, system and computer program product for biometric enclosed space control. In an embodiment of the invention, a method for biometric enclosed space control includes establishing a set point for an enclosed space and electronically transmitting a directive to a temperature control system to heat an atmosphere in the enclosed space to maintain a temperature of the atmosphere at the set point. The method also includes detecting a presence of an end user in the enclosed space and remotely sensing biometric measurements of the end user, while the end user remains in the enclosed space. In this regard, the end user refers to any living organism including but not limited to a human being. Finally, the method includes electronically transmitting a directive to the temperature control system to change the set point in response to a most recently received one of the remotely sensed biometric measurements.

In one aspect of the embodiment, a command is electronically transmitted to the temperature control system to introduce cool fluid into the enclosed space in response to a most recently received one of the remotely sensed biometric measurements. In another aspect of the embodiment, a command is electronically transmitted to the temperature control system to introduce warm fluid such as hot air or hot steam or hot water into the enclosed space in response to a most recently received one of the remotely sensed biometric measurements. In another aspect of the embodiment, the directive is electronically transmitted on condition that the most recently received one of the remotely sensed biometric measurements exceeds a threshold value, or in the alternative, on condition that the most recently received one of the remotely sensed biometric measurements indicates a threshold change from a past received one of the remotely sensed biometric measurements that exceeds a threshold value. To with, the threshold value may be based on the health condition of an end user present in the enclosed space, such as heat stroke or other temperature dependent stress. In even yet another aspect of the embodiment, the remotely sensed biometric measurements of the end user are received wirelessly from a smart watch affixed to the end user.

In another embodiment of the invention, an enclosed space control data processing system is configured for biometric enclosed space control. The system includes a host computing platform communicatively linked to a temperature control system of an enclosed space. The platform includes one or more computers, each with memory and at least one processor. The system also includes a biometric enclosed space control module. The module includes program code that when executing in the memory of the platform is enabled to establish a set point for the enclosed space and electronically transmit a directive to the temperature control system to o maintain a temperature of an atmosphere in the enclosed space at the set point, detect a presence of an end user in the enclosed space, remotely sense biometric measurements of the end user while the end user remains in the enclosed space, and electronically transmit a directive to the temperature control system to change the set point in response to a most recently received one of the remotely sensed biometric measurements, for example to cool or heat the atmosphere.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 1 is a pictorial illustration of a process for biometric enclosure temperature control;

FIG. 2 is a schematic illustration of an enclosure control data processing system configured for biometric enclosure temperature control; and, FIG. 3 is a flow chart illustrating a process for biometric enclosure temperature control.

DETAILED DESCRIPTION

Embodiments of the invention provide for biometric enclosure temperature control. In accordance with an embodiment of the invention, a temperature regulation system for an enclosed space, such as a heating system, can be activated and the atmosphere contained therein temperature regulated to a set point. The temperature regulation can be heating and can occur by way of dry heating or humidified heating. In the former instance, air is heated through a heating element such as a radiator or fire place. In the latter instance, steam is introduced into the enclosed space. Alternatively, the temperature regulation can be cooling and can occur by way of introducing cool air through air condition or a fan, or through the introduction of cool misting. In either circumstance, a presence of an end user in the enclosed space is then detected and a biometric measurement of the end user remotely sensed, for instance a temperature of the end user by way of temperature sensor, or a pulse by way of a heartbeat monitor. On condition that the remotely sensed biometric measurement exceeds a threshold value, or on condition that the remotely sensed biometric measurement reflects a threshold change from a previously remotely sensed biometric measurement, the set point is reduced and, optionally, cooled fluid such as cold air, cold mist or cold water is introduced into the enclosed space, or in the alternative, heated fluid such as hot air or steam or hot water is introduced into the enclosed space.

In further illustration, FIG. 1 pictorially shows a process for biometric enclosed space control. As shown in FIG. 1, a temperature control system 160 heats water in an enclosed space 110 to a set point and maintains the temperature of the water in the enclosed space 110 at the set point. In this regard, the closed space may be a room, sheltered area or defined geographically defined area including any partially or fully enclosed space, as well as any receptacle or vessel that can retain a fluid, such as aquariums, terrariums, hot tubs, pools, and the like. Biometric enclosed space control logic 140 then detects a presence of an end user 120, such as a human being or any other living organism, in the enclosed space 110. Biometric data 130 for the end user 120 thereafter is received periodically, for instance a skin temperature of the end user 120 or a pulse measurement of the end user 120. The biometric data 130 may be received wirelessly over short range radio frequency link between an accessory worn by the end user 120 such as a smart watch, or temperature measuring ear device, or general temperature sensor, and the biometric enclosed space control logic 140.

Biometric enclosed space control logic 140 evaluates the biometric data 130 to determine if a threshold value has been exceeded by the biometric data 130 or a change in the biometric data 130, or a rate of change in the biometric data 130. On condition that the threshold value has been exceeded by the biometric data 130, or by a change in the biometric data 130 between a most recent measurement and past measurements, or a rate of change in the biometric data 130, the biometric enclosed space control logic 140 transmits a directive 150 to the temperature control system 160 to change the temperature of the enclosed space 110, such as by activating an air cooling system, cooling misting system or by introducing cool water to the enclosed space 110, or by activating an air heating system, steamer or by introducing hot water into the enclosed space 110. However, to the extent that the threshold value is not exceeded, the directive 150 may instruct the temperature control system 160 to continue to regulate the enclosed space 110 at the set point.

Of note, the biometric enclosed space control logic 140 may read from temperature control system 160 not just the set point, but a duration of time during which the enclosed space 110 is to remain activated, a time when the enclosed space 110 first activated and thus a time at which the regulation of the temperature of the enclosed space 110 as the set point is to discontinue. Consequently, the biometric enclosed space control logic 140 may determine from the biometric data 130 a threshold rate of change predictive of an impending measurement of biometric data 130 likely to exceed the threshold value so as to necessitate a directing of the changing of temperature of the atmosphere in the enclosed space 110. In response to detecting a threshold rate of change of the biometric data 130, the biometric enclosed space control logic 140 computes a time at which the biometric data 130 is likely to exceed the threshold value based upon the detected threshold rate of change.

Then, the biometric enclosed space control logic 140 computes an estimated lower set point of the enclosed space 110 so as to reduce the rate of change of the biometric data 130 so as to cause the time at which the biometric data 130 is likely to exceed the threshold value beyond the time when the regulation of the temperature of the enclosed space 110 is to discontinue. Finally, the biometric enclosed space control logic 140 transmits a directive 150 to the temperature control system 160 to change the temperature of the atmosphere of the enclosed space 110 to the estimated lower set point.

The process described in connection with FIG. 1 may be implemented in connection with a data processing system. In further illustration, FIG. 2 schematically illustrates an enclosed space control data processing system configured for biometric enclosed space control. The system includes a host computing platform 210 that includes one or more computers, each with memory 210B and at least one processor 210A. The host computing platform 210 is communicatively linked to a temperature control system 220 managing the temperature of an enclosed space 230. In this regard, the temperature control system 220 manages the air temperature in the enclosed space 230 by receiving a temperature reading of the air in the enclosed space from thermometer 240 and responding to the temperature by directing a heater 250 to heat the enclosed space until the atmosphere within the enclosed space reaches a set point established in the temperature control system 220. Optionally, the temperature control system 220 may direct a cooling of the enclosed space actuating a switch 260 permitting a flow of cool fluid 270 into the enclosed space 230. For instance, the switch 260 may direct the activation of an air conditioning system, or an air misting system, both enabled to cool the enclosed space with a cooled fluid such as air.

Notably, a biometric enclosed space control module 300 is coupled to the host computing platform 210. The biometric enclosed space control module 300 includes computer program instructions that when executed in the memory of the host computing platform 210, is enabled to receive in wireless biometric data receiver 280 from a wirelessly transmitting accessory, biometric data of an individual disposed within the enclosed space 230, and to compute a value for the received biometric data, such as a contemporaneous measurement of a pulse of the individual, or a contemporaneous measurement of a skin temperature of the individual. The program instructions additionally may be enabled to compute a change in value between the contemporaneous measurement of the individual and one or more past measurements. The program instructions even further may be enabled to compute a rate of change of the measurements both past and contemporaneous.

Based upon the computed value or values, the program instructions of the biometric enclosed space module 300 is enabled to respond to a crossing of a pre-determined threshold value by transmitting a directive to the temperature control system 220 to discontinue any heating operation performed by the heater 250 and instead to permit a cooling of the enclosed space 230. Optionally, the directive to the temperature control system 220 may cause the temperature control system 220 to actuate switch 260 to permit a flow of cold fluid from cold fluid supply 270 into the enclosed space 230 so as to cause a more rapid cooling of the atmosphere within the enclosed space 230. For example, the actuation of the switch 260 may permit the flow of cold water to a misting fan to produce a cold air mister, or the actuation of the switch 260 may permit the flow of cold air from an air conditioner.

In even yet further illustration of the operation of the biometric enclosed space control module 300, FIG. 3 is a flow chart illustrating a process for biometric enclosed space control. Beginning in block 310, a presence of an end user in an enclosed space is sensed and, in response, biometric data is received from the end user 320, such as a sequence of pulse measurements, or a sequence of skin temperature measurements. In block 330, a change in the measurements or a value of the most recent measurement or measurements is computed. In decision block 340, if the computed value or change in value exceeds a threshold, in block 360 a cooling directive is transmitted to the temperature control system of the enclosed space. Otherwise, in block 350, the temperature control system of the enclosed space is permitted to continue heating the water of the enclosed space to a set point.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for biometric enclosed space control, the method comprising:
    establishing a set point for an enclosed space and electronically transmitting a directive to a temperature control system to temperature regulate an atmosphere in the enclosed space to maintain a temperature of the atmosphere at the set point;
    detecting a presence of an end user in the enclosed space;
    remotely sensing biometric measurements of the end user while the end user remains in the enclosed space; and,
    electronically transmitting a directive to the temperature control system to change the set point in response to a most recently received one of the remotely sensed biometric measurements, wherein the directive is electronically transmitted on condition that the most recently received one of the remotely sensed biometric measurements indicates a threshold change from a past received one of the remotely sensed biometric measurements that exceeds a threshold value.

2. The method of claim 1, wherein a command is electronically transmitted to the temperature control system to introduce cool fluid into the enclosed space in response to a most recently received one of the remotely sensed biometric measurements.

3. The method of claim 1, wherein the directive is electronically transmitted on condition that the most recently received one of the remotely sensed biometric measurements exceeds a threshold value.

4. The method of claim 1, wherein the remotely sensed biometric measurements of the end user are received wirelessly from a smart watch affixed to the end user.

5. The method of claim 1, wherein the remotely sensed biometric measurements include skin temperature measurements.

6. The method of claim 1, wherein the remotely sensed biometric measurements include pulse measurements.

7. The method of claim 1, wherein the directive is additionally electronically transmitted on condition that the most recently received one of the remotely sensed biometric measurements is predictive of an impending measurement that is likely necessitate the change in the set point.

8. The method of claim 7, further comprising computing a time at which the remotely sensed biometric measurements are likely to exceed the threshold value based upon a rate of change of the remotely sensed biometric measurements.

9. The method of claim 8, further comprising:
    establishing a set point duration for the enclosed space; and
    electronically transmitting a directive to the temperature control system to maintain the temperature of the atmosphere at the set point for the set point duration.

10. An enclosed space control data processing system configured for biometric enclosed space control, the system comprising:
    a host computing platform communicatively linked to a temperature control system of an enclosed space, the platform comprising one or more computers, each with memory and at least one processor; and,
    a biometric enclosed space control module comprising program code that when executing in the memory of the platform is enabled to:
        establish a set point for the enclosed space and electronically transmit a directive to the temperature control system to temperature regulate an atmosphere in the enclosed space to maintain a temperature of the atmosphere at the set point;
detect a presence of an end user in the enclosed space;
remotely sense biometric measurements of the end user while the end user remains in the enclosed space; and,
electronically transmit a directive to the temperature control system to change the set point in response to a most recently received one of the remotely sensed biometric measurements, wherein the directive is electronically transmitted on condition that the most recently received one of the remotely sensed biometric measurements indicates a threshold change from a past received one of the remotely sensed biometric measurements that exceeds a threshold value.

11. The system of claim 10, wherein a command is electronically transmitted to the temperature control system to introduce cool fluid into the enclosed space in response to a most recently received one of the remotely sensed biometric measurements.

12. The system of claim 10, wherein the directive is electronically transmitted on condition that the most recently received one of the remotely sensed biometric measurements exceeds a threshold value.

13. The system of claim 10, wherein the remotely sensed biometric measurements include skin temperature measurements.

14. The system of claim 10, wherein the remotely sensed biometric measurements include pulse measurements.

15. A computer program product for biometric enclosed space control, the computer program product comprising a computer readable storage medium having program instructions embodied therewith, wherein the computer readable storage medium is not a transitory signal per se, the program instructions executable by a device to cause the device to perform a method comprising:

establishing a set point for an enclosed space and electronically transmitting a directive to a temperature control system to temperature regulate an atmosphere in the enclosed space to maintain a temperature of the atmosphere at the set point;
detecting a presence of an end user in the enclosed space;
remotely sensing biometric measurements of the end user while the end user remains in the enclosed space; and,
electronically transmitting a directive to the temperature control system to change the set point in response to a most recently received one of the remotely sensed biometric measurements, wherein the directive is electronically transmitted on condition that the most recently received one of the remotely sensed biometric measurements indicates a threshold change from a past received one of the remotely sensed biometric measurements that exceeds a threshold value.

16. The computer program product of claim 15, wherein a command is electronically transmitted to the temperature control system to introduce cool fluid into the enclosed space in response to a most recently received one of the remotely sensed biometric measurements.

17. The computer program product of claim 15, wherein the directive is electronically transmitted on condition that the most recently received one of the remotely sensed biometric measurements exceeds a threshold value.

18. The computer program product of claim 15, wherein the remotely sensed biometric measurements of the end user are received wirelessly from a smart watch affixed to the end user.

19. The computer program product of claim 15, wherein the remotely sensed biometric measurements include skin temperature measurements.

20. The computer program product of claim 15, wherein the remotely sensed biometric measurements include pulse measurements.

* * * * *